July 14, 1964 S. D. McGREDY IV Plant Pat. 2,424
ROSE PLANT
Filed Aug. 23, 1963
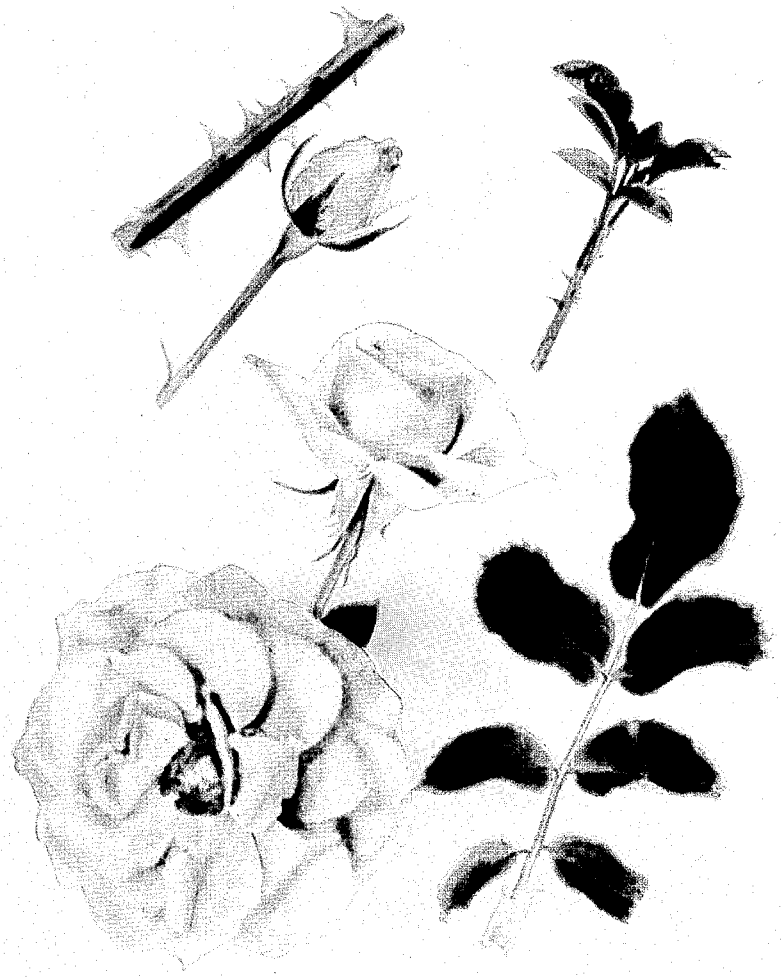
Inventor.
S. D. McGredy, IV
By: Robb & Robb
Attorneys United States Patent Office Plant Pat. 2,424
Patented July 14, 1964

2,424
ROSE PLANT

Samuel D. McGredy IV, Portadown, Ireland, assignor to Jackson & Perkins Company, Newark, N.Y., a corporation of New York Filed Aug. 23, 1963, Ser. No. 304,284
1 Claim. (Cl. Plt.—28)

The present invention relates to a new and distinct variety of rose plant of the floribunda class, which was originated by me by crossing the variety known as "Moulin Rouge" (U.S. Plant Patent No. 1,298) with the variety known as "Korona" (unpatented).

The primary objective of this breeding was to modify the parent variety "Moulin Rouge" by combining therein the larger flower size and rich flower color of the parent variety "Korona." This objective was fully achieved, along with other desirable improvements, as evidenced by the following unique combination of characteristics which are outstanding therein and which distinguish the new variety from its parents, as well as from all other varieties of which I am aware:

(1) A well balanced and broad plant habit, with the plants attaining an average height of about 2½ feet and having the habit of being constantly in bloom;

(2) A habit of bearing large clusters of long-lasting flowers, with the trusses being much larger than those of either parent, and the flowers being more lasting than those of either parent;

(3) A distinctive and attractive general color tonality of the flowers corresponding to Scarlet-Red, lightly overcast with Spectrum Red, this coloration being quite distinct and different from the flower color of either parent variety; and (4) A flower habit characterized by easy shattering of the spent flowers, thus leaving clean flower clusters at all times.

Asexual reproduction of my new variety by budding, as performed, in Ireland, as well as at Newark, New York, and Pleasanton, California, U.S.A., shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Moulin Rouge."
*Pollen parent.*—"Korona."
Classification:
*Botanic.*—Floribunda.
*Commercial.*—Floribunda.

*Flower*

(Observations made from specimens grown outdoors at Newark, New York, U.S.A., in the early morning during the early part of the month of September.)
Blooming habit: Recurrent—continuous.
Bud:
*Size.*—Medium.
*Form.*—Ovoid; is not affected by wet or hot weather.
*Color.*—When sepals first divide—Carmine, Plate 1. When petals begin to unfurl—Carmine, Plate 1, lightly overcast with Spectrum Red, Plate 1. When half-blown: inside of petals—Spectrum Red, Plate 1, very lightly overcast with Scarlet-Red, Plate 1; reverse of petals—Nopal Red, Plate 1, very lightly overcast with Spectrum Red, Plate 1.
*Sepals.*—Slightly branched; curl back when petals begin to unfurl. Color: inside—Yellowish Glaucous, Plate 41; outside—Light Elm Green, Plate 17, lightly overcast with Carmine, Plate 1.
*Calyx.*—Color—Pois Green, Plate 41, very lightly overcast with Carmine, Plate 1. Shape—pear. Size — small. Aspect — smooth. Odor when rubbed—none.
*Peduncle.* — Length — short. Aspect — smooth. Strength—erect; slender. Color—deep Chrysolite Green, Plate 31, very lightly overcast with Acajou Red, Plate 13.
*Openings.*—Opens up well; is not affected by adverse whether conditions.
Bloom:
*Size.*—Medium. Average size when fully expanded—3 inches.
*Borne.*—Several together and in large, rounded clusters which are constantly in flower.
*Stems.*—Medium length; strong.
*Form (when first open).*—Cupped. Permanence—flattens.
*Petalage.*—Semi-double (two rows of petals). Number of petals under normal conditions—from 10 to 12.
*Color.*—Center of flower—Spectrum Red, Plate 1, lightly overcast with Scarlet-Red, Plate 1. Outer petals—Scarlet-Red, Plate 1. Base of petals (aiglet)—Pale Lemon Yellow, Plate 4. Inside of petals—Scarlet-Red, Plate 1, lightly overcast with Spectrum Red, Plate 1. Reverse of petals—Nopal Red, Plate 1, overcast with Spectrum Red, Plate 1. General tonality from a distance—Scarlet-Red, Plate 1, overcast with Spectrum Red, Plate 1.
*Discoloration.*—General tonality at end of first day—Spectrum Red, Plate 1, lightly overcast with Scarlet-Red, Plate 1. Second day—Spectrum Red, Plate 1, overcast with Scarlet-Red, Plate 1. Third day—Spectrum Red, Plate 1, overcast with Scarlet-Red, Plate 1.
Petals:
*Texture.*—Leathery; is not affected by wet or hot weather.
*Appearance.*—Inside—velvety. Outside—satiny.
*Form.*—Oval; slightly scalloped.
*Arrangement.*—Imbricated (regularly arranged shingle-like).
*Petaloids in center.*—Few, small.
*Persistence.*—Spent flowers drop off cleanly.
*Fragrance.*—Moderate. Nature—tea (average hybrid tea scent).
*Lasting quality.*—On plant—long. As cut flower—long.

*Genital Organs*

Stamens, anthers: Medium size; many; regularly arranged arranged styles. Color—Amber Yellow, Plate 16.
Stamens, filaments (threads): Short. Color—Orient Pink, Plate 2.
Pollen: Color—Straw Yellow, Plate 4.
Styles: Loosely separated; uneven length; medium length; thin.
Stigmas: Color—Shell Pink, Plate 28.
Ovaries: All enclosed in calyx.
Hips: None.
Seeds: None.

*Plant*

Form: Bush; broad; well balanced.
Growth: Vigorous; upright; branching; attains average height of about 2½ feet.

Foliage: Compound of 5–7 leaflets.

*Size.*—Medium.

*Quantity.*—Normal.

*Color.*—New foliage: upper side—Acajou Red, Plate 13; under side—Ocher Red, Plate 27. Old foliage: upper side—Varley's Green, Plate 18; under side—Dark Olive Buff, Plate 40.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; small.

*Leaf stem.*—Color—Tea Green, Plate 47, lightly overcast with Eugenia Red, Plate 13. Under side—smooth.

*Stipules.*—Medium length; bearded.

Wood:

*New wood.*—Color—Shamrock Green, Plate 32, very lightly overcast with Ocher Red, Plate 27. Bark—smooth.

*Old wood.*—*Color*—Cress Green, Plate 31. Bark—smooth.

Thorns:

*Thorns.*—Quantity: on main stalks from base—many; on laterals from stalks—many. Form—flat base; medium length; some straight and some hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combinaiton of a well balanced and broad plant habit, with the plant ataining an average height of about 2½ feet and being constantly in flower, a habit of bearing large custers of long-lasting flowers, a distinctive and attractive general color tonality of the flowers corresponding to Scarlet-Red, lightly overcast with Spectrum Red, and an easily shattering habit of the spent flowers which results in clean clusters at all times.

No references cited.